US 6,702,683 B2

(12) United States Patent
Abrams et al.

(10) Patent No.: US 6,702,683 B2
(45) Date of Patent: Mar. 9, 2004

(54) METERING AND PACKAGING OF CONTROLLED RELEASE MEDICATION

(75) Inventors: Andrew L. Abrams, Westport, CT (US); Anand V. Gumaste, Robbinsville, NJ (US)

(73) Assignee: Microdose Technologies, Inc., Monmouth Junction, NJ (US)

( * ) Notice: Subject to any disclaimer, the term of this patent is extended or adjusted under 35 U.S.C. 154(b) by 0 days.

(21) Appl. No.: 10/044,612

(22) Filed: Jan. 11, 2002

(65) Prior Publication Data

US 2002/0142035 A1 Oct. 3, 2002

Related U.S. Application Data

(63) Continuation of application No. 09/376,619, filed on Aug. 18, 1999, now Pat. No. 6,428,809.

(51) Int. Cl.[7] .............................. A61K 9/20; A61K 9/22; A61K 9/44; A61K 9/28
(52) U.S. Cl. ...................... 464/465; 464/450; 464/464; 464/467; 464/468; 464/474
(58) Field of Search ................. 424/450, 464, 424/465, 467, 468, 474

(56) References Cited

U.S. PATENT DOCUMENTS

| 3,241,625 | A |   | 3/1966  | Soojian .................... 177/120 |
|-----------|---|---|---------|-------------------------------------|
| 3,437,074 | A |   | 4/1969  | Hagopain et al. ........... 118/623 |
| 3,889,636 | A |   | 6/1975  | Smith ....................... 118/621 |
| 3,943,437 | A |   | 3/1976  | Mourier ..................... 324/32 |
| 3,977,323 | A |   | 8/1976  | Pressman et al. ........... 101/426 |
| 3,999,119 | A |   | 12/1976 | Bares ........................ 324/32 |
| 4,021,587 | A |   | 5/1977  | Banker ...................... 427/18 |
| 4,071,169 | A |   | 1/1978  | Dunn ......................... 222/76 |
| 4,170,287 | A |   | 10/1979 | Edwards et al. ............ 198/657 |
| 4,197,289 | A | * | 4/1980  | Sturzenegger et al. ......... 424/21 |
| 4,204,766 | A |   | 5/1980  | Harada ....................... 356/404 |
| 4,252,434 | A |   | 2/1981  | Nakamura et al. ............. 355/15 |
| 4,255,777 | A |   | 3/1981  | Kelly ......................... 361/228 |
| 4,339,428 | A | * | 7/1982  | Tencza ........................ 424/21 |
| 4,379,969 | A |   | 4/1983  | Cobb et al. ................. 250/324 |
| 4,399,699 | A |   | 8/1983  | Fujishiro ..................... 73/304 |
| 4,514,781 | A |   | 4/1985  | Plasschaert et al. ......... 361/230 |
| 4,555,174 | A |   | 11/1985 | Kramer ................... 355/3 DD |
| 4,594,901 | A |   | 6/1986  | Norman ................... 73/861.04 |
| 4,626,876 | A |   | 12/1986 | Miyagawa et al. .......... 346/160 |
| 4,734,722 | A |   | 3/1988  | Maczuszenko et al. ...... 346/159 |
| 4,795,644 | A | * | 1/1989  | Zentner ...................... 424/468 |
| 4,848,267 | A |   | 7/1989  | Slayton et al. ............. 118/653 |
| 4,875,060 | A |   | 10/1989 | Masuda et al. ............. 346/155 |
| 4,878,454 | A |   | 11/1989 | Cann ......................... 118/663 |
| 5,005,516 | A |   | 4/1991  | Speer ......................... 118/657 |
| 5,009,894 | A | * | 4/1991  | Hsiao ......................... 424/451 |

(List continued on next page.)

FOREIGN PATENT DOCUMENTS

| EP | 0431924     | 1/1996  | ........... B29C/67/24 |
| EP | 0 885 662 A1 | 12/1998 | ........... B05D/1/06  |
| EP | 0 891 817 A2 | 1/1999  | ........... B05B/5/08  |
| JP | 4277126     | 10/1992 | ........... 198/690.01 |
| WO | 9800337     | 1/1998  | ........... B65B/1/30  |
| WO | WO 98/42446 | 10/1998 | ........... B05B/5/025 |

OTHER PUBLICATIONS

US 5,585,099, 12/1996, Sun et al. (withdrawn)
Science News, vol. 151, p. 205, "Ink jets not just for the printed page". (Apr. 5, 1997).

Primary Examiner—Thurman K. Page
Assistant Examiner—S. Tran
(74) Attorney, Agent, or Firm—Hayes Soloway P.C.

(57) ABSTRACT

Controlled quantities of powdered medication are formed in controlled release packages using electrostating metering. Also provided are combination medication therapy delivery packages comprising two or more active pharmaceuticals segregated from one another in a single delivery package.

9 Claims, 4 Drawing Sheets

U.S. PATENT DOCUMENTS

| | | | |
|---|---|---|---|
| 5,074,426 A | * 12/1991 | Goodhart et al. | 220/4.24 |
| 5,102,045 A | 4/1992 | Diana | 239/3 |
| 5,204,055 A | 4/1993 | Sachs et al. | 419/2 |
| 5,214,386 A | 5/1993 | Singer et al. | 324/452 |
| 5,404,871 A | 4/1995 | Goodman et al. | 128/200.14 |
| 5,421,816 A | 6/1995 | Lipkovker | 604/20 |
| 5,454,271 A | 10/1995 | Yamamoto et al. | 73/861.04 |
| 5,490,962 A | 2/1996 | Cima et al. | 264/22 |
| 5,508,040 A | * 4/1996 | Chen | 424/451 |
| 5,655,523 A | 8/1997 | Hodson et al. | 128/315 |
| 5,669,973 A | 9/1997 | Pletcher | 118/624 |
| 5,699,649 A | 12/1997 | Abrams et al. | 53/428 |
| 5,714,007 A | 2/1998 | Pletcher et al. | 118/629 |
| 5,827,538 A | 10/1998 | Cussler et al. | 424/473 |
| 5,960,609 A | * 10/1999 | Abrams et al. | 53/428 |
| 6,009,690 A | * 1/2000 | Rosenberg et al. | 53/454 |
| 6,013,280 A | * 1/2000 | Frisbee et al. | 424/464 |
| 6,027,748 A | * 2/2000 | Conte et al. | 424/458 |
| 6,032,871 A | 3/2000 | Borner et al. | 239/3 |
| 6,319,541 B1 | * 11/2001 | Pletcher et al. | 427/2.14 |

* cited by examiner

METERING AND PACKAGING OF CONTROLLED RELEASE MEDICATION

CROSS REFERENCE TO RELATED APPLICATION

This application is a continuation of our Application Ser. No. 09/376,619 filed Aug. 18, 1999 now U.S. Pat No. 6,428,809.

FIELD OF THE INVENTION

The present invention relates to the packaging of dry powders and particularly to the metering and packaging of precise quantities of pharmaceuticals and drugs for medical uses. The invention has particular utility in the metering and packaging of dry powders, particularly precise amounts of dry powder pharmaceuticals and drugs, and will be described in connection with such utility, although other utilities are contemplated.

BACKGROUND OF THE INVENTION

The convenience of administering a single dose of a medication which releases multiple active ingredients in a controlled fashion and in a chosen location over an extended period of time, as opposed to the administration of a number of single doses at regular intervals, has long been recognized in the pharmaceutical arts. The advantage to the patient and clinician in having consistent and uniform blood levels of medication over an extended period of time are likewise recognized. The advantages of a variety of controlled-release dosage forms are well known. Among the most important advantages are: (1) increased contact time for the drug to allow for local activity in the stomach, small intestine, colon, or other locus of activity; (2) increased and more efficient absorption for drugs which have specific absorption sites; (3) the ability to reduce the number of dosages per period of time; (4) employment of less total drug; (5) minimization or elimination of local and/or systemic side effects; (6) minimization of drug accumulation associated with chronic dosing; (7) improved efficiency and safety of treatment; (8) reduced fluctuation of drug level; and (9) better patient compliance with overall disease management.

Additionally, many experts believe controlled release drug delivery has many important non-therapeutic ramifications as well, including a financial saving to the patient in terms of fewer lost work days, reduced hospitalization and fewer visits to the physician.

It is known that certain design parameters are critical to proper drug delivery. Typically, they are: (1) delivering the drug to the target tissue; (2) supplying the drug for a predetermined period of time; and (3) fabricating a delivery system that provides drug in the desired spatial and temporal pattern. Controlled release drug delivery systems are intended to utilize these parameters to achieve the aforementioned advantages as compared to conventional pharmaceutical dosing.

Previously direct placement of medication onto a substrate generally was limited to medical placement of large doses or required technology where the active pharmaceutical was mixed with the substrate or matrix to provide differential delivery, or coated with a material with desired release characteristics.

As used herein "controlled-release" is used to describe a system, i.e. method and materials for making an active ingredient available to the patient in accordance with a preselected condition, i.e. time, site, etc.. Controlled-release includes the use of instantaneous release, delayed release and sustained release. "Instantaneous release" refers to immediate release to the patient. "Delayed release" means the active ingredient is not made available until some time delay after administration. Typically, dosages are administered by oral ingestion, although other forms of administration are contemplated in accordance with the present invention. "Sustained release" refers to release of active ingredient whereby the level of active ingredient available to the patient is maintained at some level over a period of time. The method of effecting each type of release can be varied. For example, the active-ingredient can be placed on a semi-permeable membrane having predetermined diffusion, dissolution, erosion or breakdown characteristics.

Alternatively, the active ingredient can be masked by a coating, a laminate, etc. Regardless of the method of providing the desired release pattern, the present invention contemplates delivery of a controlled-release system which utilizes one or more of the "release" methods and materials. Moreover, the present invention advantageously can be employed in the development of multiple different release system(s).

The patent and scientific literature is replete with various sustained release (SR) methods and materials. For common methods of obtaining SR systems, see "Sustained and Controlled Release Drug Delivery Systems," Robinson, Joseph R., Ed., PP 138–171, 1978, Marcel Dekker, Inc. New York, N.Y. For example it is known to fill polymeric capsules with a solid, liquid, suspension or gel containing a therapeutic agent which is slowly released by diffusion through the capsule walls. Heterogeneous matrices, for example, compressed tablets, control the release of their therapeutic agents either by diffusion, erosion of the matrix or a combination of both. Other SR systems focus on the fabrication of laminates of polymeric material and therapeutic agent which are then formed into a sandwich, relying on different diffusion or erosion rates to control release of the therapeutic agent. Liquid-liquid encapsulation in a viscous syrup-like solution of polymer also has been known to be useful in controlling release of the therapeutic agent. Additionally, it is generally known that heterogeneous dispersions or solutions of therapeutic agents in water-swellable hydrogen matrices are useful in controlling the release of the agent by slow surface-to-center swelling of the matrix and subsequent diffusion of the agent from the water-swollen part of the matrix.

During dissolution of a controlled-release matrix tablet, the dosage form generally remains as a non-disintegrating, slowly eroding entity from which the therapeutic agent leaches out, through a diffusion controlled process. Conventional SR formulations are generally designed to release their active ingredients over an extended period of time, usually 8–24 hours. Conventional SR formulations use waxes or hydrophilic gums as the primary drug carriers to prolong the release of the active ingredients.

Starch USP (potato or corn) is commonly used as a component in conventional tablet or hard shell capsule formulations.

The existing sustained release technologies generally involve relatively complicated formulations and manufacturing processes which often are difficult and expensive to precisely control. For example, one well known SR delivery system, OROS, marketed by the Alza Corporation, involves laser drilling through a tablet to create passages for the release of the drug from the tablet core. In controlled release technologies, it is desirable to be able to incorporate the active ingredient in its controlled-release pattern in a single dosage unit without deteriorating the active ingredient. Moreover, the dosage unit should be able to deliver the system without interfering with its release pattern.

Various methods have been devised to enable controlled-release systems to be delivered to a patient without destruction of the delivery system during manufacturing, handling and distribution. For example, controlled-release systems have been provided in the form of beads or particles which are packaged in a gelatin capsule for oral dosage. This method of delivery of the controlled-release system prevents damage to the coating on the beads.

Furthermore, when controlled-release active ingredients are incorporated in compression tablets, it may be difficult for many people to swallow such tablets. Moreover, dissolution of high compression tablets often initially is slow and erratic and may result in localized hot spots of alimentary tract irritation where disintegration and release of the active ingredient finally occurs. And, present systems do not allow for the accurate deposition of doses of powdered medication onto different substrates either in single packets, layered packet, or multipackets on the same plane of the base substrate. The present invention overcomes the disadvantages of the prior art by offering a simple and inexpensive means of incorporating active ingredient (the drug) with a multitude of controlled-release systems.

In our earlier U.S. Pat. No. 5,699,649, granted Dec. 23, 1997, we describe a method and apparatus for packaging microgram quantities of fine powders such as pharmaceuticals using electrostatic phototechnology techniques. More particularly, as described in our aforesaid U.S. Pat. No. 5,699,649, the ability of powders to acquire an electrical charge advantageously is utilized for precisely measuring exact microgram quantities of the powder, whereupon these exact microgram quantities are then placed in individual containers, and the containers sealed.

Electrostatic charge has been employed to attract a given quantity of powder to a surface. An example of this is the laser printer or the electrostatic copy device where a drum is charged and toner particles are attracted and held in position by the charge. The charge on the drum is neutralized by the attracted toner powder, thus limiting the amount of toner in accordance with the charge image on the drum. The charged powder on the printer drum is then transferred to a sheet of paper or other carrier to give a final image. In our U.S. Pat. No. 5,699,649, electrostatic charge technology is employed for transferring a predetermined amount of a finely powdered pharmaceutical or drug to a carrier or an intermediate such as a drum, carrying a charge of predetermined intensity and area, rotating the charged drum surface, carrying the predetermined amount of powdered pharmaceutical or drug on its surface, to a transfer station where the charge is overcome and the dry powder is transferred to a package which is then sealed. In lieu of a drum, a belt, or other movable surface is charged to a given potential in a localized area. Alternatively, a predetermined amount of powdered pharmaceutical or drug may be deposited directly in a package using electrostatic charge technology.

When a given amount of a powdered pharmaceutical or drug is to be packaged, the charge and area of charge can be determined experimentally for each dose of pharmaceutical or drug and each particle size distribution. This can be done by controlling either the charged area for a given charge density or the total electrostatic charge on any individual charged area. These conditions can be adjusted to provide essentially the exact desired amount of the particular pharmaceutical or drug to be transferred at the transfer station.

In our U.S. application Ser. No. 09/097,104, we describe another electrostatic charge technology which may be adopted to be used for measuring and packaging unit doses of a pharmaceutical or drug in a readily ingestible form, i.e. as a tablet or capsule. The technology thus described also permits reproducible precise measurement and packaging of a pharmaceutical or drug, and which may be scaled from laboratory to pilot plant to full scale production without the need for recertification.

BRIEF DESCRIPTION OF THE INVENTION

In accordance with one aspect of the present invention, controlled quantities of powdered medication are formed in controlled release packages using electrostatic metering technology. The present invention also provides, in another aspect, combination medication delivery systems in which the active ingredients are segregated from one another

BRIEF DESCRIPTION OF THE DRAWINGS

Further features and objects of the present invention will become clear from the following detailed description taken in conjunction with the accompanying drawings, wherein like numerals depict like parts, and wherein.

DETAILED DESCRIPTION OF THE INVENTION

Figure 1:
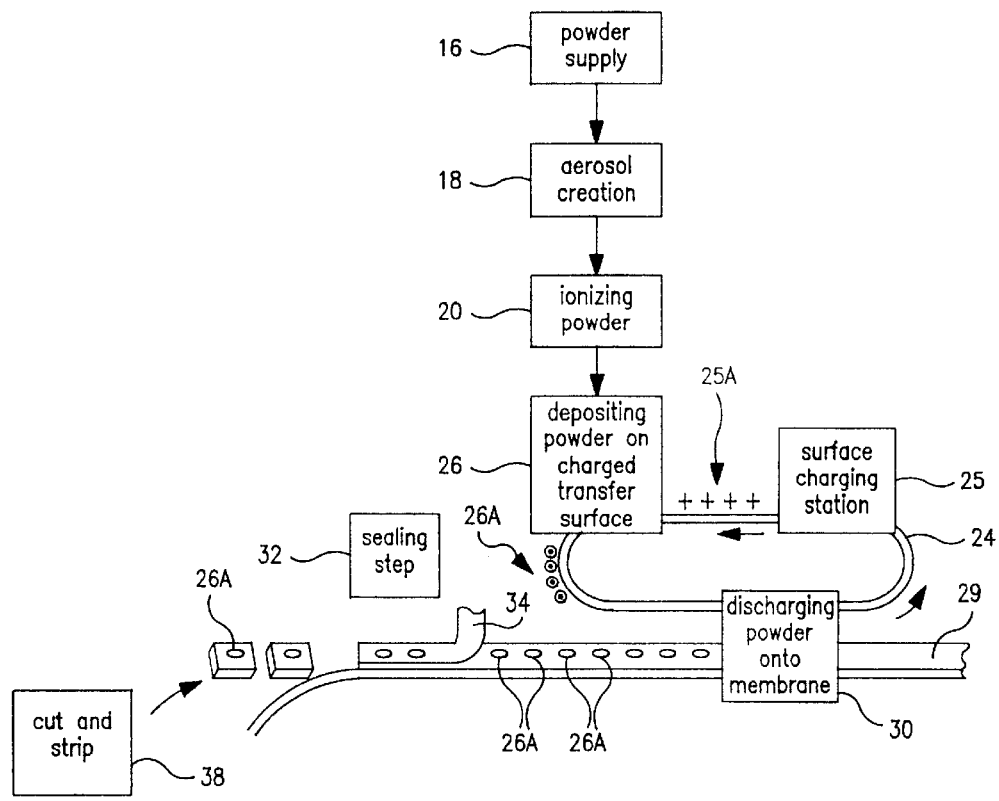
FIG. 1 is a schematic flow diagram showing the various steps involved in practicing the present invention.
Figure 2:
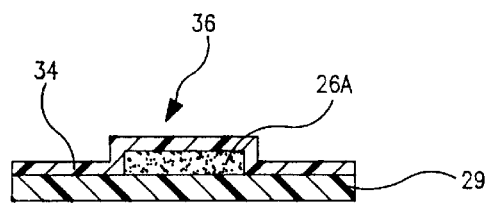
FIG. 2 is an enlarged cross-sectional view of one embodiment of a controlled release tablet made in accordance with the present invention.

Referring now to FIG. 1, there is a schematic flow diagram of the various pieces of equipment needed to perform in the total process from powder supply to packaged pharmaceutical or drug, i.e. in controlled release tablet form, containing a specified amount of pharmaceutical or drug powder in the tablet or package. At 16 is indicated the pharmaceutical or drug powder supply which is fed into a device 18 for creating an aerosol of the powder. Next the powder particles are ionized at 20. As will be indicated later, a number of these steps and pieces of equipment can be combined. At 24 is indicated a carrier surface capable of maintaining a space charge on its surface. This can be a plastic belt, for example, or a selenium drum of the type used in Xerox™ photocopiers. This carrier surface 24 is passed through a charging station 25 where a predetermined electrostatic charge 25A (an electrostatic "image") is created on a predetermined area of the transfer surface. This charged surface 25A then passes through a step 26 wherein powder is deposited on the carrier surface in a sufficient amount 26A to neutralize the charge carried by the carrier surface.

Thereafter, the carrier surface, carrying the predetermined amount 26A of powder on its surface, is passed to a powder discharging device 30 which discharges the powder 26A from the surface 24 onto a membrane 29. Alternatively, the powder may be placed directly onto the membrane 29. The membrane 29 containing its charge of powder 26A, then passes through a sealing step 32 wherein a second membrane 34 which may be porous, permeable or semipermeable covers and seals the discharged powder 26A on the membrane 29. There is thus produced an aliquot of powdered medicine 26A sandwiched between semipermeable or permeable membranes 29 and 34.

This sandwiched material is then passed to a cutting station 38 wherein the sandwich is cut into individual tablets or wafers 36.

As mentioned previously in discussing FIG. 1, the carrier surface with the electrostatic charge carries a known amount of charge on its surface and the polarity of this charge is opposite to that of the powder particles suspended in the chamber. The charged particles migrate to the charged surface because of the attraction by the opposite nature of the charges. This migration of the particles continues until the charge on the carrier surface is neutralized.

The actual amount of powder mass transferred to the carrier surface is a function of the mass-to-charge ratio of the charged particles. Although it is difficult to achieve a linear relationship between the mass and the actual charge, it is possible to establish a fixed relationship between the surface area of the powder particles and the charge the powder particle is carrying at charge saturation. However, the surface area of a mixed group of powder particles of different sizes and shapes can be extremely difficult to calculate mathematically, particularly when the shapes are irregular, (e.g. non-spherical, microcrystalline, etc.) As mentioned earlier, the simplest method of determining the amount and area of charge to attract a given weight of particles is to estimate the correct area and charge and then apply the estimated charge to the estimated area on the carrier surface 24 and expose this selectively charged area to a mass of powder which has been ionized in the ionizing step. The amount of powder deposited can then be readily measured at the discharge step. Thereafter, either the size of the charged area or the amount of charge applied to the area at the charging station 25 can be adjusted upwardly or downwardly to provide the correct amount of charge, both in area and charge intensity, for picking up a desired weight of oppositely charged powder. Likewise, using the technology of our co-pending application Ser. No. 09/097,104, larger quantities of medication may be deposited.

A feature and advantage of the present invention is to produce carefully controlled doses of controlled release medication. Electrostatic metering and packaging as above described permits exact dosing. And, by employing selected porous, permeable or semi-permeable membranes for encapsulating the powdered medicine aliquots, drug release rate and also site of drug release can be determined by adjusting membrane material and/or membrane thickness.

The membranes should be formed of ingestible materials having a selected permeability porosity to fluids at a selected site or sites within the alimentary canal, so as to permit controlled release of the medication. By way of example, one or both membranes 29, 34 may comprise acid-dissolvable materials when it is desired to release the medication into the stomach or the membranes 29, 34 may be alkaline-dissolvable materials at differing pH's to release into chosen locations within the intestine. Porosity, membrane thickness, etc., may be selected to provide desired rate of dissolution at the site of interest.

Figure 4:
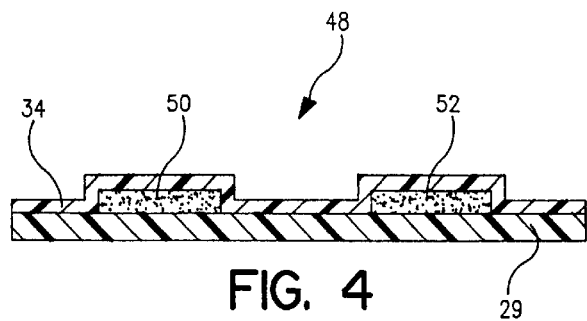
FIG. 4 is a view, similar to FIG. 2, and showing an alternative form of a controlled release tablet made in accordance with the present invention.
Figure 3:
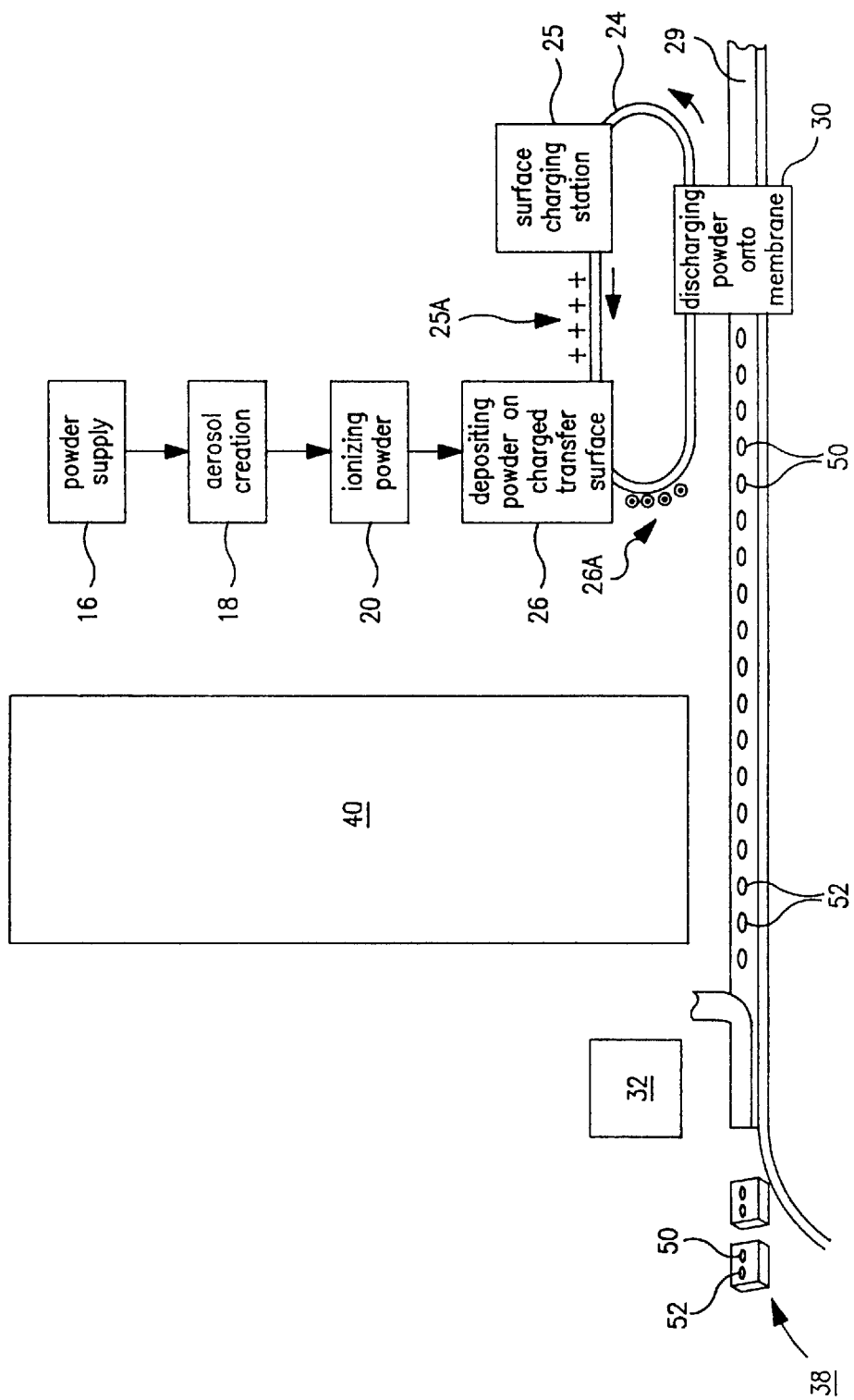
FIG. 3 is a view, similar to FIG. 1, and showing alternative steps involved in practicing the present invention.
Figure 5:
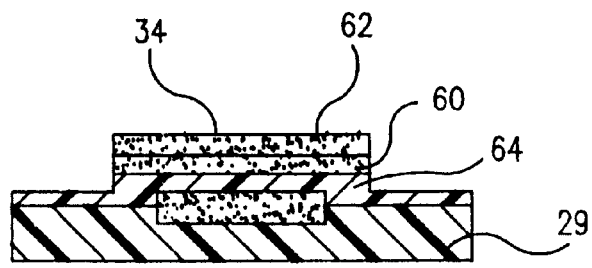
FIG. 5 is a view similar to FIG. 2, and showing yet another alternative embodiment of the present invention.

The invention is susceptible to modification. For example, referring to FIGS. 3 and 4 by adding a second powdered medicine supply and discharge station (shown generally at 40), a two-component controlled release tablet 48 may be formed (see FIG. 4) incorporating two different powdered medicines 50, 52, encapsulated between membranes 29 and 34 for simultaneous controlled release. Alternatively, as shown in FIG. 5, two different drugs 60, 62 may be layered on one another, separated by a membrane 64 so the two medications may be delivered sequentially either in the same location, or in different locations within the alimentary canal. Another feature and advantage of the multi-drug tablet of FIG. 4 and FIG. 5, as will be discussed in detail herein below, is that two normally incompatible drugs may be to be safely packaged in a single tablet.

The invention is susceptible to modification. For example, individual doses may be formed by electrostatic deposition in accordance with U.S. Pat. No. 5,714,007.

Figure 6:
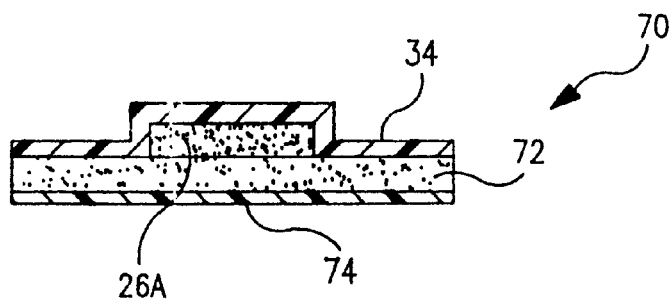
FIG. 6 is a view, similar to FIG. 2, and showing yet another embodiment of the invention.

Other possibilities are possible. For example, referring to FIG. 6, the tablet 70 may incorporate an adhesive layer 72 such as a mucosal adhesive, which in turn is covered by an acid or alkaline dissolvable protective membrane 74, which dissolves at a selected site allowing the adhesive to adhere, for example, to the intestinal wall, thereby increasing residence time of the medication in a chosen location. Alternatively, an acid or alkaline activatable adhesive may be applied to the outer surface of the tablet. In yet another possibility, the membrane may be a material which expands on contact with the acid or alkaline in the alimentary canal and becomes more porous whereby to slowly release medication in a chosen location within the alimentary canal.

As mentioned above, a particular feature and advantage of the present invention is that it permits packaging, within a single tablet of two or more different drugs normally considered to be incompatible. Certain drugs are known to cause undesirable side effects which need to be countered by a second drug. For example, Omeprazole[1] which finds substantial utility as an oral antiulcer agent, also is known to block the release of B12 from its protein binding site in food. This can lead to pernicious anemia. The present invention permits packaging of time-release Omeprazole with Vitamin B12 in an appropriate dosage of, e.g. 25 $\mu$m–1 mg. After taking the medication, one membrane will dissolve allowing absorption of the B12, while the remaining membrane package carrying the Omeprazole will pass into the small intestine where the drug is released and absorbed.

Figure 7:
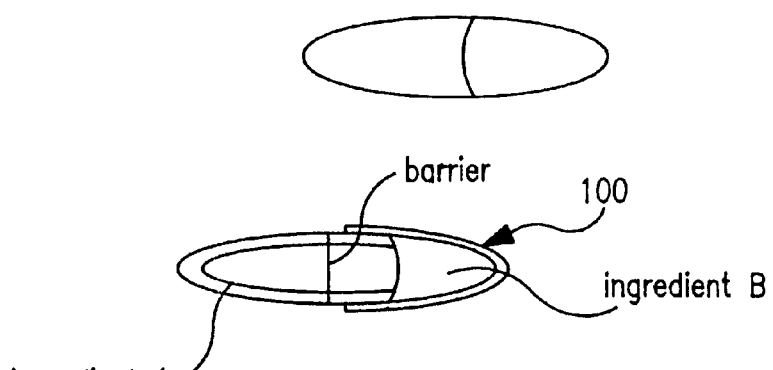
FIGS. 7–9 are views similar to FIG. 2, and showing yet other embodiments of the present invention.
Figure 8:
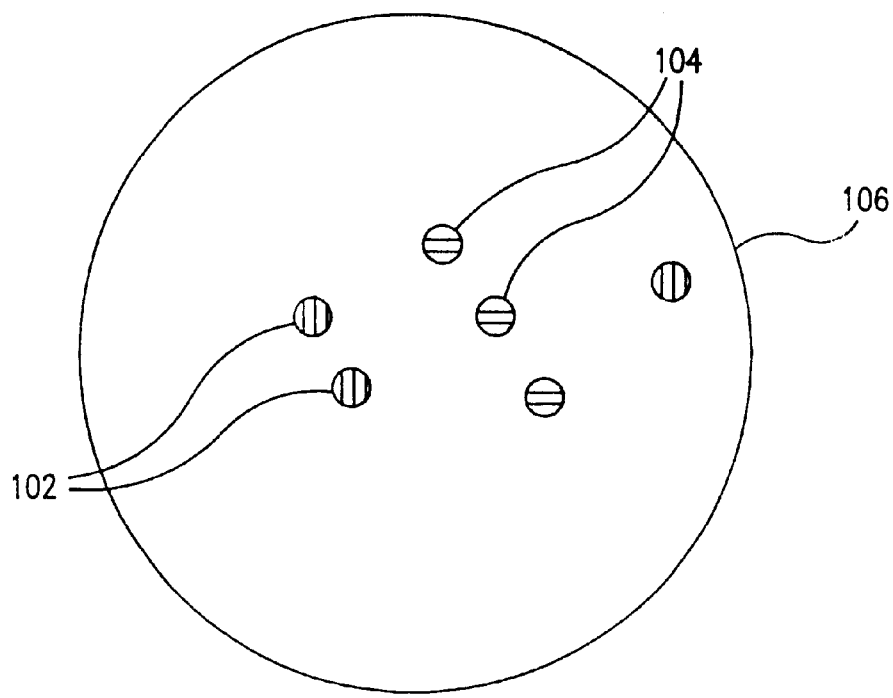
Figure 9:
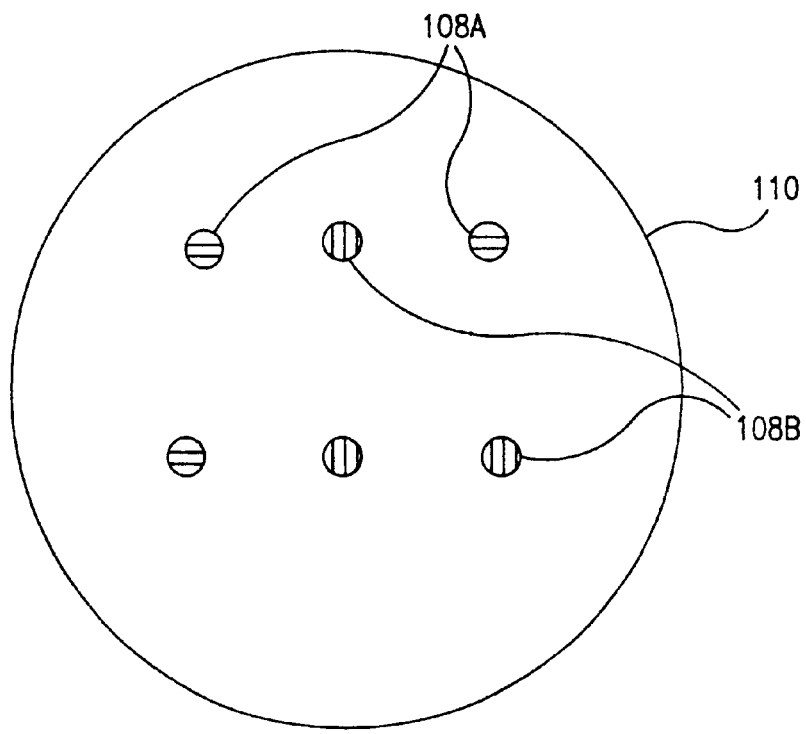

The invention is susceptible to modification. For example, while the membranes have been described as being preformed, permeable, semipermeable or porous material, one or both membranes could be formed in place from a gel or liquid. The ability to accurately place the dose of medication onto a plurality of substrates and seal the dose with other membranes in accordance with the present invention, allows for the fabrication of many different dosage forms; by altering the substrates and encapsulating material a single unit dose form can be fabricated with a plurality of different drugs in different coverings, membranes and barriers. This will provide a single dosage form with multiple active ingredients each being delivered to the appropriate site for absorption. Alternatively, two or more active medicaments may be combined in a single delivery container, i.e. pill, capsule or caplet without actually mixing the two or more ingredients. For example, referring to FIG. 7, the active ingredients are segregated from one another in a compartmentalized capsule 100. Alternatively, two or more tablets 102, 104 each containing only one active ingredient, could be placed in a larger absorbable capsule or encased in a larger tablet 106. Or, as shown in FIG. 9, two or more active ingredients could each be formulated as encapsulated particles 108A, 108B, and the encapsulated mixed particles placed in a capsule 110 where the only contact is between the particle inert coatings, etc.

There are many drugs which could benefit from combinations to improve patient benefit. However, with many active ingredients, there is a question of chemical interaction. Thus, several drugs are normally prescribed as separate tablets or capsules which presents a problem in terms of patient compliance, e.g. TB triple therapy, AIDS multi-drug therapy, anti-infectives, etc. Also, delivery of two or more active medicaments could reduce side effects, and/or improve therapeutic response which may in turn permit a decrease in the required dosage. By way of example, we provide the following combinations:

(1) Omeprazole[1] and analogs and isomers—As noted above Omeprazole is an inhibitor of gastric secretion and also inhibits the absorption of certain drugs/compounds that require stomach acid such as Vitamin B12, the deficit of which results in pernicious anemia. A combination of B12 with Omeprazole would eliminate the potential problem.

(2) Valacyclovir[2] and analogs and is used to treat Herpes Zoster. It is well known that two$^{drugs}$ Cimetidine[3] and Probenecid[4] both increase the AUC (area under curve) and Cmax. A combination drug can be constructed with a combination of either one or more of these components to provide more efficacy.

(3) Enalapril[5] and analogs and isomers is an ACE inhibitor used for the treatment of hypertension. This drug has been used with the following and analogs and isomers beta adrenegic-blocking agents, methyldopa, nitrate, calcium blocking agents, hydrazinc, Prazosin[6] and Digoxin[7] without clinically significant side effects. One or more of these agents may be combined with Enalapril to improve the compliance of patient with hypertension and hypertension and other cardiac diseases.

(4) Ketoconazole[8] and analogs and isomers is used to treat fungal infections. One of the side effects is the reduction of Testosterone. This side effect could be helped by the combination of Testosterone or one of its isomers or analogs to overcome the side effect.

(5) Omeprazole[1] and analogs and isomers is also used in combination with Clarithoromycin[1] for ulcer treatment. These two drugs may be combined as a single dose for patient compliance.

(6) Tamoxifen[10] and analogs and isomers used in treatment of breast cancer has a +/−30% incident of water retention with weight gain >5%. This can be a disturbing consequence for patients with an even more disturbing disease. The addition of a diuretic or combination diuretic to form a single dosage form for reduction in side effect and compliance.

(7) Isotretinoin[11] and analogs and isomers used for the treatment of postular acne has a severe danger if taken by a woman who is pregnant. The incorporation of oral contraceptive medication would eliminate the potential for pregnancy while medicated.

(8) Metformin HCl[12] and analogs and isomers are hypoglycemic agents which have been used in combination with Solfonylurea[13] and analogs and isomers to treat Type 2 Diabetes. These two agents act in different ways on reducing glucose levels. A combination would be helpful for those patients requiring more aggressive oral therapy for their diabetes.

It should be noted that certain combination drugs, including some of the above-listed combination drugs, also may be blended and packaged in a single tablet or capsule, when chemical interaction is not a problem.

The present invention also allows for the rapid production of different dosage medications using the same active ingredient, and allows for the development of medications with longer resident time.

What is claimed is:

1. A controlled release pharmaceutical delivery package comprising unit aliquot doses of two or more different active pharmaceuticals combined in a single delivery package, segregated from one another, electrostatically deposited on a porous, permeable or semi-permeable ingestible membrane, and formed into a tablet, wherein said two or more active pharmaceuticals comprise combinations of pharmaceuticals selected from the group consisting of (a) Ketoconazole and testosterone, (b) Valacylovir and one or both of Cimetidine and Probenecid, (c) Enalapril and a beta adrenergic-blocking agent, methyldopa, nitrate, a calcium blocking agent, hydrazinc, Prazosin or Digoxin, (d) Omeprazole and B12, (e) Omeprazole and Clarithoromycin, (f) Tamoxifen and a diuretic, (g) Isotretinoin and an oral contraceptive, and (h) Metformin HCI and Solfonylurea.

2. A pharmaceutical delivery package according to claim 1, wherein said membrane comprises an acid-dissolvable material.

3. A pharmaceutical delivery package according to claim 1, wherein said membrane comprises an alkali-dissolvable material.

4. A pharmaceutical delivery package according to claim 1, wherein said two or more pharmaceuticals are separated by one another by one or more barriers or membranes.

5. A pharmaceutical delivery package according to claim 1, and further comprising an adhesive on the outer surface of the membrane.

6. A pharmaceutical delivery package according to claim 5, wherein the adhesive is acid or alkylene activatable.

7. A pharmaceutical delivery package according to claim 5, and further comprising an alkali or acid dissolvable membrane covering the adhesive.

8. A pharmaceutical delivery package according to claim 1, wherein said membrane comprises a material which expands upon contact with acid or alkaline in the alimentary canal, whereby to become more porous.

9. A pharmaceutical delivery package according to claim 1, wherein said pharmaceuticals are encapsulated within inert coatings.

\* \* \* \* \*